United States Patent [19]

Broger et al.

[11] Patent Number: 5,750,690

[45] Date of Patent: May 12, 1998

[54] ASYMMETRIC HYDROGENATION PROCESS USING RUTHENIUM-DIPHOSPHINE COMPLEXE

[75] Inventors: Emil Albin Broger, Magden; Yvo Crameri, Oberwil; Marquard Imfeld, Binningen; François Montavon, Delémont; Erich Widmer, Münchenstein, all of Switzerland

[73] Assignee: Hoffmann-La Roche Inc., Nutley, N.J.

[21] Appl. No.: 690,215

[22] Filed: Jul. 26, 1996

Related U.S. Application Data

[63] Continuation of Ser. No. 330,404, Oct. 28, 1994, abandoned, which is a continuation of Ser. No. 57,231, May 4, 1993, abandoned.

[30] Foreign Application Priority Data

May 18, 1992 [CH] Switzerland ............... 1582/92
Mar. 11, 1993 [CH] Switzerland ............... 729/93

[51] Int. Cl.$^6$ .............. C07D 237/26; C07D 237/04; C07D 231/04
[52] U.S. Cl. .............. 544/234; 544/224; 544/235; 548/356.1; 548/360.1; 548/363.1; 548/379.4; 540/496; 540/500; 540/553; 540/567
[58] Field of Search .............. 544/224, 234, 544/235; 548/356.1, 359.1, 360.1, 363.1

[56] References Cited

U.S. PATENT DOCUMENTS

| 4,331,818 | 5/1982 | Riley | 568/17 |
| 4,512,924 | 4/1985 | Attwood et al. | 540/500 |
| 4,556,740 | 12/1985 | Hansen et al. | 568/13 |

FOREIGN PATENT DOCUMENTS

| 104375 | 4/1984 | European Pat. Off. |
| 272787 | 6/1988 | European Pat. Off. |
| 398132 | 11/1990 | European Pat. Off. |

OTHER PUBLICATIONS

Bevan et al. *J. Chem. Soc.* pp. 514–522, 1971.
Adams et al, *Synthetic Communications 18* pp. 2225–2231, 1988.
Tetr.Lett. 29 Nr. 46, 5969–5972 (1988) Hayashi et al.
Liebigs Ann Chem 1974, 1391–1398 (Bormann).
Chem. and Ind. Feb. 1, 1964 p. 193 (Loev).
J. Gen. Chem. USSR 29, 95–99 (1959) (Kost et al.).
Helv. Chim. Acta 61, Fasc 4(1988) No. 135, 1364–1372 (Schiess et al.).
J. Chem. Soc. Chem Commun 1989, 1208–1210 (K. Mashima et al.).
Abstract (corresponding to EP398 132) Nov. 22, 1990.
Advanced Organic Chemistry (2nd Ed.) by Jerry Mar., pp. 92–94 (1977).
Noyori et al. Acc. Chem. Res. 23:345–350 (1990).
Abstract of JP 55061937–May 11, 1980.

*Primary Examiner*—Emily Bernhardt
*Attorney, Agent, or Firm*—George W. Johnston; Patricia S. Rocha-Tramaloni; Robert A. Silverman

[57] ABSTRACT

A process for the asymmetric hydrogenation of a compound of the formula

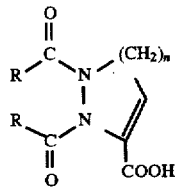

II wherein each R, independently, is alkyl, arylmethyl, aryl, alkoxy, arylmethoxy or aryloxy or both R's, taken together, are methylene, ethylene or 1,2-phenylene and n is 1,2 or 3, or of a salt thereof to a compound of the formula

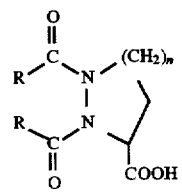

I in the form of an (S) or (R) enantiomer, wherein R and n have the significances given above, using an optically active ruthenium-diphosphine complex as catalyst, is described. The preparation of the compounds of formula II, as well as the compounds of formula II, which form a further object of the invention, are also described.

10 Claims, No Drawings

ASYMMETRIC HYDROGENATION PROCESS USING RUTHENIUM-DIPHOSPHINE COMPLEXE

This is a continuation of application Ser. No. 08/330,404 filed Oct. 28, 1994, now abandoned which is a Rule 60 Continuation of Ser. No. 08/057,231, filed May 4, 1993, now abandoned.

BRIEF SUMMARY OF THE INVENTION

The invention relates to a catalyzed process for the preparation of a compound of the formula

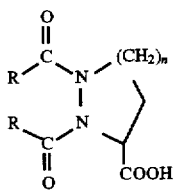

I wherein each R, independently, is alkyl, arylmethyl, aryl, alkoxy, arylmethoxy or aryloxy, or both R's, taken together, are methylene, ethylene or 1,2-phenylene and n is 1,2 or 3, in the (S)- or (R)-form,
which comprises asymmetrically hydrogenating the corresponding 3-carboxy-3-pyrazoline, 3-carboxy-1,2,5,6-tetrahydropyridazine or 3-carboxy-1,2-diaza-3-cycloheptene derivative of the formula

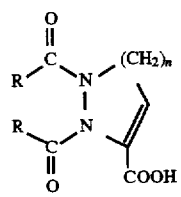

II wherein the two R's and n are as described above, or a salt thereof in the presence of an optically active ruthenium-diphosphine complex.

DETAILED DESCRIPTION OF THE INVENTION

The invention relates to a catalyzed process for the preparation of compounds of the formula

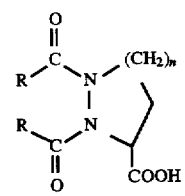

I wherein each R, independently, is alkyl, arylmethyl, aryl, alkoxy, arylmethoxy or aryloxy, or both R's, taken together, are methylene, ethylene or 1,2-phenylene and n is 1,2 or 3, in the (S)- or (R)-form,
which are valuable and in part known intermediates.

The process in accordance with the invention to prepare a compound of formula I comprises asymmetrically hydrogenating the corresponding 3-carboxy-3-pyrazoline, 3-carboxy-1,2,5,6-tetra-hydropyridazine or 3-carboxy-1,2-diaza-3-cycloheptene derivative of the formula

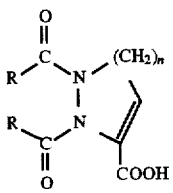

II wherein the two R's and n are as previously described, or a salt thereof in the presence of an optically active ruthenium-diphosphine complex.

The term "alkyl", used in connection with formulas I and II above, shall mean especially $C_{1-6}$-alkyl, in which the larger ($C_{3-6}$) alkyl groups can be straight-chain or branched. Exemplary of such groups are methyl, ethyl, propyl, isopropyl, n-butyl, isobutyl, tert.butyl, n-pentyl, tert.pentyl, neopentyl, n-hexyl and the like. The term "alkoxy" shall mean groups in which the alkyl residue has the meaning as set forth above. When R is aryl, it is preferably optionally substituted phenyl. The substituted phenyl can have one or more substituents, such as lower alkyl and lower alkoxy, preferably straight-chained or branched-chained alkyl or alkoxy with up to 6 carbon atoms, and halogen, for example, fluorine, chlorine, bromine or iodine. This also applies to aryl when used in the terms arylmethyl, arylmethoxy and aryloxy, which likewise fall under the definition of R.

Salts of the carboxy compounds of formula II comprise the alkali metal, alkaline earth metal and ammonium salts, for example, the sodium, potassium, calcium, magnesium or triethylammonium salt.

Further, in the scope of the present invention, the notation "━" indicates that the corresponding substituent is situated above the plane of the molecule.

Used as ruthenium catalysts (optically active ruthenium-diphosphine complexes) for the process in accordance with the invention are preferably complexes of the formulas

III and

IV wherein $X^1$ is a halide, an anion A—COO$^\ominus$ or an anion A—SO$_2$O$^\ominus$, $X^2$ is a halide, $X^3$ is benzene, hexamethylbenzene or p-cymene, $X^4$ is a halide, BF$_4{}^\ominus$, ClO$_4{}^\ominus$ or B(phenyl)$_4{}^\ominus$, m is the number 1 or 2, A is lower alkyl, halogenated lower alkyl or aryl and L is an optically active atropisomeric diphosphine ligand, especially a ligand of the formula

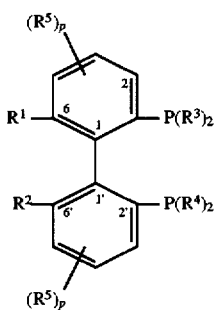

V or of the formula

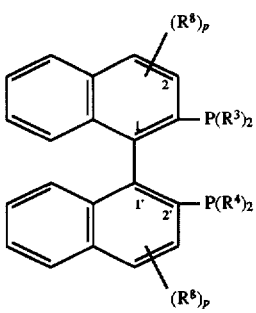

VI wherein

R¹ and R² each, independently, are lower alkyl, lower alkoxy, di(lower alkyl)amino, hydroxy, protected hydroxy, hydroxymethyl or protected hydroxymethyl or R¹ and R² taken together are a divalent group —(CH₂)_q—, —CH₂—O—CH₂—, 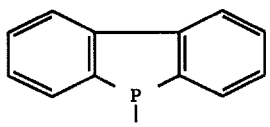

or 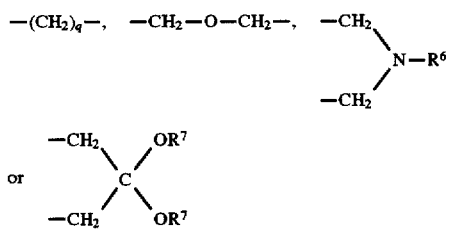

R³ and R⁴ each, independently, are lower alkyl, C₃₋₇-cycloalkyl, optionally substituted phenyl, a five-membered heteroaromatic or a group of the formula

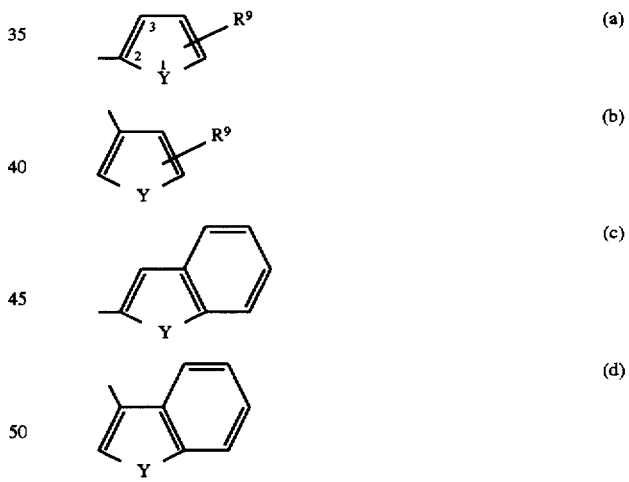

R⁵ is lower alkyl or lower alkoxy,

R⁶ is lower alkyl, optionally substituted phenyl or optionally substituted benzyl, R⁷ is lower alkyl or both R⁷'s together are di- or trimethylene, R⁸ is halogen, hydroxy, methyl, ethyl, amino, acetamido, nitro or sulfo, p is zero or the number 1,2 or 3 and q is the number 3, 4 or 5.

In formulas III–IV, the terms used therein shall have the meaning hereinafter set forth. The terms "halide" and "halogen" shall mean fluorine, chlorine, bromine or iodine. The term "lower alkyl" shall mean straight-chained or branched-chained alkyl with 1 to 4 carbon atoms, such as, methyl, ethyl, propyl, isopropyl, n-butyl, isobutyl and tert.butyl. The term "lower alkoxy" shall mean a group in which alkyl has the foregoing significance. This also applies to other groups containing "lower alkyl", for example, halogenated lower alkyl and di(lower alkyl)amino. Under the just-mentioned "halogenated lower alkyl" groups, there are to be understood lower alkyl groups which are mono- or multiply-substituted with the same or different halogen atoms, especially with fluorine and/or chlorine. Preferably, a halogen is situated in the α-position (on residue A) to the —COO⁻. Preferred halogenated lower alkyl groups are perchlorinated and perfluorinated lower alkyl groups, for example, trichloromethyl and, respectively, pentafluoroethyl. The term "aryl" is preferably phenyl, biphenyl or naphthyl which is unsubstituted or mono- or multiply-substituted with the same or different lower alkyl groups and/or halogen atoms, with perchlorophenyl and perfluorophenyl being preferred halogenated aryl groups A. When R³, R⁴ or R⁶ is optionally substituted phenyl or, with respect to R⁶ alone, optionally substituted benzyl, there come into consideration as substituents, in the case of benzyl for its phenyl moiety, particularly fluorine; lower alkyl or alkoxy, preferably methyl or methoxy; di(lower alkyl)amino, preferably dimethylamino; tri(lower alkyl)silyl, preferably trimethylsilyl; and phenyl. As protecting groups for the hydroxy or hydroxymethyl group (R¹ and/or R² as protected hydroxy or protected hydroxymethyl) there especially come into consideration the usual ether-forming groups, for example, benzyl, allyl, benzyloxymethyl, lower alkoxymethyl, (2-methoxyethoxy)-methyl and the like. The term "five-membered heteroaromatic" shall mean a substituent of the formula wherein Y is oxygen, sulfur or NR¹⁰; R⁹ is hydrogen, lower alkyl, especially methyl, or lower alkoxy, especially methoxy; and R¹⁰ is lower alkyl, especially methyl.

When p in formula VI is 1, 2 or 3, at least two residues R⁸ are, preferably, situated in the 5,5'-position.

The asymmetric hydrogenation, in accordance with the invention, of a compound of formula II or of a salt thereof, to form the corresponding compound of formula I, can be effected in a suitable organic solvent which is inert under the reaction conditions. Examples of such solvents are lower alcohols, for example, methanol and ethanol; aliphatic esters, for example, ethyl acetate; halogenated aliphatic hydrocarbons, for example, methylene chloride; cyclic ethers, for example, tetrahydrofuran and dioxane; water; and mixtures of the above solvents. The hydrogenation is conveniently carried out at temperatures between about 0° C. and about 150° C., preferably in the temperature range of about 20° C. to about 100° C., and at a pressure of about 1 to about 100 bar, preferably of about 5 to about 40 bar. The percentage molar ratio of ruthenium in the ruthenium catalyst to a compound of formula II or to its salt which is to be hydrogenated (the "substrate") conveniently lies between about 0.0005 and about 5, corresponding to a molar ratio substrate to catalyst (S/C) of about 200,000 to about 20, preferably between about 0.001 and about 0.01 (S/C about 100,000 to about 10,000).

Where a salt of the compound of formula II is used as the starting material, it can be used as such or can be generated in situ, for example, by adding about one molar equivalent, based on the amount of educt, of a base to the hydrogenation medium. Especially suitable bases are alkali and alkaline earth metal hydroxides, for example, sodium hydroxide, potassium hydroxide or calcium hydroxide; tert.ammonium hydroxides, for example, triethylammonium hydroxide; quaternary ammonium hydroxides, for example, tetramethylammonium hydroxide or tetrabutylammonium hydroxide; and alkylamines, for example, triethylamine.

The work-up, even in the case of a salt, is generally effected in a simple manner, for example, by crystallization from the partially concentrated hydrogenation solution which has been acidified using a mineral acid, for example, hydrochloric acid. The product can be obtained in good purity by recrystallization.

The optically active ruthenium-diphosphine complexes, for example, those of formulas III and IV, are either known or can be produced in a known manner, for example in analogy to the procedures described in European Patent Publication 397,042 and in J. Chem. Soc. Chem. Commun. 1989, 1208–1210 (K. Mashima et al.). The ligands of formulas V and VI are known, for example, from European Patent Publications 104,375 and 398,132 or from Japanese Patent Publication (Kokai) 136,605/1978, or can be obtained in analogy to the preparation of known ligands. The publications relate to methods for the preparation of those ligands of formulas V and VI in which $R^3$ and $R^4$ are the same. Compounds in which $R^3$ and $R^4$ are different from each other can be obtained analogously thereto, although in two steps, for example, according to the following Reaction Scheme:

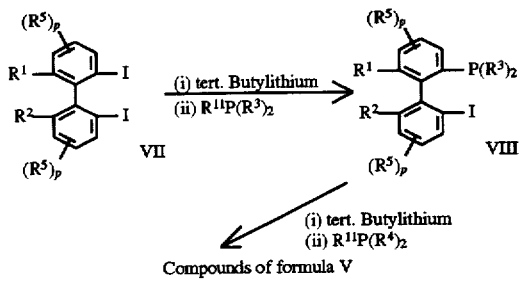

Compounds of formula V wherein $R^1$, $R^2$, $R^3$, $R^4$, $R^5$ and p have the above significances and $R^{11}$ is a leaving group, for example, halogen, especially chlorine or bromine; or alkoxy, especially methoxy or ethoxy. In order to guarantee that only one iodine atom is replaced by a lithium atom, the corresponding reactions are conveniently carried out using about equivalent amounts of reaction partners.

In carrying out the asymmetric hydrogenation in accordance with the invention, an optically active ruthenium-diphosphine complex, for example, that of formula III or IV,
can first be produced, and then a solution of a compound of formula II or salt thereof to be hydrogenated is added thereto. Alternatively, the ruthenium catalyst can be produced in situ, optionally in the presence or absence of the compound to be hydrogenated.

The 3-carboxy-3-pyrazoline, 3-carboxy-1,2,5,6-tetrahydropyridazine and 3-carboxy-1,2-diaza-3-cycloheptene derivatives of formula II and their salts, which are used as starting materials in the process in accordance with the invention, also form part of the invention. They can be produced, for example, in accordance with the following Reaction Scheme:

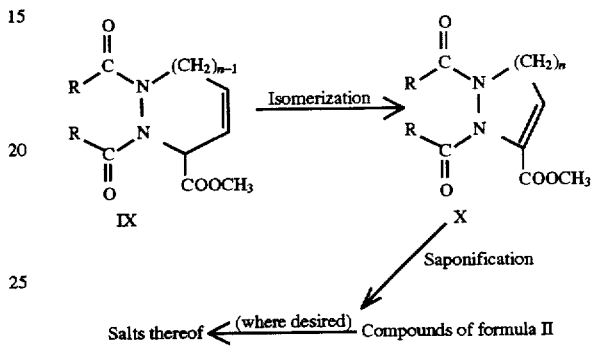

wherein R and n have the significances given above. The compounds of formula IX are either known or can be produced according to known methods.

The isomerization of the compound of formula IX to the compound of formula X is conveniently effected in an organic solvent at temperatures of about room temperature to the reflux temperature of the reaction mixture and, moreover, in the presence of a base. An especially suitable organic solvent is a cyclic ether, for example, dioxane or tetrahydrofuran, or an aromatic hydrocarbon, for example, toluene, and an especially suitable base is 1,5-diazabicyclo[4.3.0]non-5-ene, 1,8-diazabicyclo[5.4.0]undec-7-ene or potassium tert.butylate.

The subsequent saponification is conveniently carried out under the influence of acetic acid or formic acid. The reaction mixture is suitable saponified in the presence of catalyst such as, for example, trifluoromethanesulfonic acid, hydrochloric acid, hydrobromic acid, sulfuric acid, methanesulfonic acid, trifluoroboron etherate or trimethylsilyl trifluoromethanesulfonate and at temperatures between about 60° C. and the reflux temperature of the reaction mixture. Conveniently, a 4–120% molar amount of catalyst is used based on the amount of educt, that is, compound of formula X.

If the compound of Formula II is not produced immediately in the form of a salt, the thus-obtained compound of formula II can be converted into the desired salt in a known manner. Similarly in a known manner, a thus-obtained salt of the compound of formula II can be converted into the corresponding compound of formula II.

As an alternative to the isomerization of a compound of formula IX, a compound of formula X can be produced according to the following Reaction Scheme:

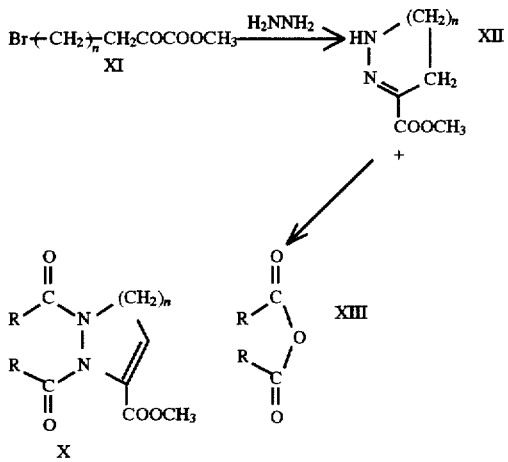

wherein R and n have the significances given above. The compounds of formula XI are either known or can be produced according to known methods.

The hydrazine used in the first step (XI→XII) of the alternative process is especially hydrazine hydrate, although a hydrazine salt, for example, the hydrochloride or the hydrosulfate, can also be used. The respective reaction is conveniently effected in an alcoholic solvent at temperatures of about 0° C. to the reflux temperature of the reaction mixture and, moreover, optionally in the presence of a base. Especially suitable alcoholic solvents are methanol, ethanol, isopropanol or an aqueous mixture of such an alcohol, for example, a mixture of methanol and water which consists of up to 90 weight percent, preferably of from 10 to 25 weight percent, of water. When a base is used, this is preferably a lower trialkylamine, for example, triethylamine; a nitrogen-containing heterocycle, for example, pyridine; an alkali metal carbonate or bicarbonate, for example, potassium carbonate or sodium bicarbonate; or an alkali metal hydroxide, for example, sodium hydroxide. Potassium carbonate has been found to be especially suitable for this purpose. A reaction temperature of about 5° C. and a pH range of 4 to 7 have been found to be favorable conditions for the hydrazone formation involved in the reaction. This pH range is conveniently attained by the initial addition of hydrochloric acid or preferably acetic acid to the hydrazine hydrate solution and by the slow addition of potassium carbonate solution during the reaction. In order to promote the subsequent conversion of the intermediately formed hydrazone into the cyclic compound of formula XII, the reaction mixture is conveniently heated to reflux temperature at the same pH value, whereby here the slow addition of an additional amount of base can be required.

The subsequent reaction of the compound of formula XII with the acid anhydride of formula XIII, for example, phthalic anhydride (both R's form 1,2-phenylene), is a condensation involving the cleavage of water. This reaction is conveniently effected under the influence of thionyl chloride, with or without base, or of acetic anhydride in the presence of a base, in an organic solvent and at temperatures between about room temperature and the reflux temperature of the reaction mixture. An especially suitable base is a lower trialkylamine, for example, triethylamine, or a nitrogen-containing heterocycle, for example, pyridine. The solvent which is used is suitably a lower chlorinated hydrocarbon, for example, methylene chloride, a lower aliphatic ester, for example, ethyl acetate, or an aromatic hydrocarbon, for example, toluene. Methylene chloride is preferably used.

In all of the process steps described above, the work-up and isolation of the respective product is effected in a known manner.

The process for the production of the starting materials of formula II, both multi-stage processes, comprises another object of the invention.

The hydrogenation process in accordance with the invention enables the compounds of formula I to be prepared in high optical purity. It is especially preferred for the preparation of (S)-1,2,3,4,6, 11-hexahydro-6,11-dioxo-pyridazino [1,2-b]phthalazine-1-carboxylic acid, i.e. the compound of formula I, in which both R's taken together are 1,2-phenylene and n is 2, that is, of the formula

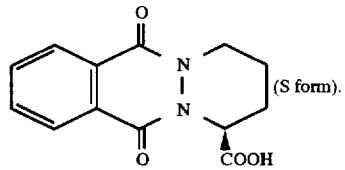

This compound is a valuable intermediate in the synthesis of the antihypertensive agent known by the name "cilazapril".

The following Examples further illustrate the invention. In the Examples, the abbreviations used have the following meaning:.

| | |
|---|---|
| OAc | acetyloxy; |
| TFA | trifluoroacetyloxy; |
| COD | (Z,Z)-1,5-cyclooctadiene; |
| CC | Capillary gas chromatography; the samples are silylated with bistrimethylsilylacetamide and chromatographed on a PVMS-54 Permaphase column (Perkin-Elmer); |
| e.e. | enantiomeric excess. The e.e. of the hydrogenation product is determined by high pressure liquid chromatography (HPLC) on an α-APG column ("α-acid glycoprotein, chiral-AGP" from Chromtek, Sweden); |
| o.p. | optical purity; |
| S/C | substrate/catalyst molar ratio; |
| Dehydrophthaloylic acid | 3,4,6,11-tetrahydro-6,11-dioxo-pyridazino-[1,2-b]phthalazine-1-carboxylic acid; |
| (S) acid | (S)- or (R)-1,2,3,4,6,11-hexahydro-6,11-dioxo-pyridazino[1,2-b]phthalazine-1-carboxylic acid; |
| (R) acid | |
| BIPHEMP | (6,6'-dimethylbiphenyl-2,2'-diyl)bis(diphenyl-phosphine); |
| MeOBIPHEP | (6,6'-dimethoxybiphenyl-2,2'-diyl)bis(diphenylphosphine); |
| (3,4,5-MeO)-MeOBIPHEP | (6,6'-dimethoxybiphenyl-2,2'-diyl)bis[di-(3,4,5-trimethoxyphenyl)phosphine]; |
| ThienylBIPHEMP | (6,6'-dimethylbiphenyl-2,2'-diyl)bis[di-(2-thienyl)phosphine]; |
| TriMeOBIPHEP | (4,4',5,5',6,6'-hexamethoxybiphenyl-2,2'-diyl)bis-(diphenylphosphine); |
| DiMeOBIPHEP | (5,5',6,6'-tetramethoxybiphenyl-2,2'-diyl)bis-(diphenylphosphine); |
| BIPHOMP | (5,7-dihydro-dibenz[c,e]oxepin-1,11-diyl)bis-(diphenylphosphine); |
| p-TolMeOBIPHEP | (6,6'-Dimethoxybiphenyl-2,2'-diyl)bis[di-(p-tolyl)phosphine]; |
| p-TolBIPHEMP | (6,6'-dimethylbiphenyl-2,2'-diyl)bis[di-(p-tolyl)phosphine]; |
| pTolBINAP | (1,1'-binaphthyl-2,2'-diyl)bis[di-(p-tolyl)-phosphine]; |
| Cy₄MeOBIPHEP | (6,6'-dimethoxybiphenyl-2,2'-diyl)bis(dicyclo-hexylphosphine). |

In the Examples, all temperatures are given in degrees Celsius (°C.).

EXAMPLE 1 a) 16.5 mg (0.0192 mmol) of Ru(OAc)₂[(S)-p-TolMeOBIPHEP] are dissolved in 50 ml of methanol at 20° in a 50 ml measuring flask in a glove box (oxygen content<1 ppm) and the solution is stirred for 2 minutes, whereby a clear, orange solution (the catalyst solution) forms.

b) A 500 ml autoclave is charged in a glove box (oxygen content<1 ppm) with 8.0 g (31.0 mmol) of dehydrophthaloylic acid, 3.14 g (31.0 mmol) of triethylamine, 148 ml of methanol and 2 ml of the aforementioned catalyst solution. The hydrogenation is carried out at 60°, a constant pressure of 40 bar of pure hydrogen and with vigorous stirring. After one hour, the conversion is 100% according to GC. The yellow hydrogenation solution is evaporated to a weight of 25 g on a rotary evaporator at 50°/220 mbar. 4.42 ml of 25% hydrochloric acid solution and subsequently 27 ml of water are added dropwise to the residual solution with stirring at 20°–35°. The (S)-acid begins to precipitate at about 25°. The suspension is stirred at 20° for 1 hour and at 0° for 1 hour. After filtration and drying there are obtained 7.7 g (96%) of (S)-acid as almost white crystals, $[\alpha]_{436}=-833.0°$ (c=1, methanol); optical purity 98.9%; 100% e.e.

EXAMPLES 2–11

Hydrogenations are carried out using a ruthenium catalyst of formula III $[Ru(X^1)_2L]$ analogously to the procedure described in Example 1 in order to convert the dehydrophthaloylic acid into the (S)-acid. The respective catalyst, the S/C, the hydrogenation time the optical purity (o.p.) or the enantiomeric excess (e.e.) are given in the following Table.

TABLE

| Example | Catalyst used Ru(X¹)₂L | | S/C | Hydrogenation time to achieve 100% conversion, in hours | o.p. % or e.e. % |
|---|---|---|---|---|---|
| | X¹ | L | | | |
| 2 | OAc | (S)-ThienylBIPHEMP | 30,000 | 20 | 97.8 (o.p.) |
| 3 | OAc | (S)-BIPHOMP | 30,000 | 5 | 98.6 (o.p.) |
| 4 | OAc | (S)-TriMeOBIPHEP | 30,000 | 5 | 97.3 (o.p.) |
| 5 | OAc | (S)-DiMeOBIPHEP | 30,000 | 5 | 98.6 (o.p.) |
| 6 | OAc | (S)-MeOBIPHEP | 40,000 | 5 | 98.9 (o.p.) |
| 7 | OAc | (S)-(3,4,5-MeO)MeOBIPHEP | 20,000 | 5 | 98.5 (o.p.) |
| 8 | OAc | (S)-pTolBINAP | 40,000 | 20 | 98.7 (o.p.) |
| 9 | OAc | (S)-pTolBIPHEMP | 40,000 | 5 | 98.5 (o.p.) |
| 10 | CH₃SO₂O | (S)-BIPHEMP | 400 | 1 | 98.6 (o.p.) |
| 11 | TFA | (S)-pTolMeOBIPHEP | 50,000 | 20 | 96.4 (e.e.) |

The above o.p. values are those of the crystallized (S)-acid, while for Example 11 the e.e. value is that of the crude product. In Examples 2–10, the yields of crystalline acid are between 90% and 95%.

EXAMPLE 12

25.35 mg (0.0775 mmol) of RU(COD)(OAc)₂ and 47.0 mg (0.0775 mmol) of (S)-CY₄MeOBIPHEP are dissolved in 6 ml of diethyl ether and 2 ml of tetrahydrofuran in a 50 ml Schlenk tube in a glove box (oxygen content<1 ppm) and the solution is stirred at 40° for 1.5 hours. A clear, red catalyst solution forms and this is used in the hydrogenation.

The hydrogenation and work-up are effected as described in Example 1b).

There are obtained 7.4 g (92%) of (S)-acid as almost white crystals, 99.2% e.e.

EXAMPLE 13

68.8 mg (0.0775 mmol) of [Ru((S)-MeOBIPHEP)(p-cymene)-Cl]Cl are dissolved in 50 ml of methanol at 20° in a glove box (oxygen content<1 ppm) and the solution is stirred for 10 minutes. A clear, orange-red catalyst solution forms and is used in hydrogenation.

The hydrogenation and work-up are effected as described in Example 1b).

There are obtained 7.3 g (91%) of (S)-acid as almost white crystals, 100% e.e.

EXAMPLE 14

77.49 mg (0.0775 mmol) of [Ru((S)BIPHEMP)(p-cymene)-CH₃CN][BF₄]₂ are dissolved in 50 ml of methanol at 20° in a glove box (oxygen content<1 ppm) and the solution is stirred for 10 minutes. A clear, orange-red catalyst solution forms and is used in the hydrogenation.

The hydrogenation and work-up are effected as described in Example 1b).

There are obtained 6.8 g (85%) of (S)-acid as almost white crystals, 98.8% e.e.

EXAMPLE 15

10.63 mg (0.0124 mmol) of Ru(OAc)₂[(S)-p-TolMeOBIPHEP] are dissolved 50 ml of methanol at 20° in a glove box (oxygen content<1 ppm) and the solution is stirred for 10 minutes, whereby a clear, orange catalyst solution forms.

A 500 ml autoclave is charged with 32.0 g (123.9 mmol) of dehydrophthaloylic acid, 12.54 g (123.9 mmol) of triethylamine, the aforementioned catalyst solution, an additional 13 ml of methanol and 7 ml of water. The hydrogenation is carried out at 60°, a constant pressure of 7 bar of pure hydrogen and with vigorous stirring. After 20 hours the conversion is 100% according to GC. In order to liberate the (S)-acid, an aliquot of the hydrogenation solution containing 0.5 g of (S)-acid is diluted with methanol and allowed to flow through an Amberlyst® 15 column. The column is rinsed with methanol until all of the acid has been eluted. The e.e. value of the crude acid (0.5 g) is 99.5%.

EXAMPLE 16

13.3 mg (0.0155 mmol) of Ru(OAc)₂[(S)-pTolMeOBIPHEP] are dissolved in 50 ml of methanol at 20° in a 50 ml measuring flask in a glove box (oxygen content<1 ppm) and the solution is stirred for 10 minutes, whereby a clear, orange catalyst solution forms.

Subsequently, a 500 ml autoclave is charged in the glove box with 8.0 g (31.0 mmol) of dehydrophthaloylic acid, 140 ml of methanol and 10 ml of the aforementioned catalyst solution. The hydrogenation is carried out at 60°, a constant pressure of 7 bar of pure hydrogen and with vigorous stirring. After 23 hours, the conversion is 98% according to GC. The yellow, slightly turbid hydrogenation solution is filtered over Celite® (diatomaceous earth), evaporated on a rotary evaporator at 50°/220 mbar and the pale yellow, crystalline (S)-acid is dried at 60°/0.01 mbar. The yield of (S)-acid is 7.7 g (96%), its e.e. value is 99.1%.

EXAMPLE 17

A 500 ml autoclave is charged in a glove box (oxygen content<1 ppm) with 64.0 g (247.8 mmol) of dehydrophthaloylic acid, 25.08 g (247.8 mmol) of triethylamine, 87.5 ml of methanol and 4.97 mg (0.0062 mmol) of Ru(OAc)$_2$[(R)-MeOBIPHEP]. The hydrogenation is effected at 100° C. and a constant pressure of 40 bar of pure hydrogen. After a hydrogenation time of 6 hours, the conversion is 100% according to GC. The hydrogenation solution is then partially evaporated and the (R)-acid is precipitated as the hydrogenation product by the dropwise addition of 34.4 ml of 25% hydrochloric acid and 216 ml of water. There are thus obtained 61.1 g (94.7% of theory) of (R)-acid as white crystals, 100% e.e.

EXAMPLE 18 a) 10.14 mg (0.031 mmol) of di($\eta^2$-acetato)-($\eta^4$-cycloocta-1,5-diene)ruthenium(II) [B. Heiser et al., Tetrahedron: Asymmetry 2, 51 (1991)] and 13.83 mg (0.031 mmol) [(S)-6,6'-dimethoxybiphenyl -2,2'-diyl]bis (diisopropylphosphine) are dissolved in 6 ml of diethyl ether and 2 ml of tetrahydrofuran in a glove box (oxygen content<1 ppm) and the solution is stirred at 40° for 1.5 hours. A clear, red catalyst solution forms.

The [(S)-6,6'-dimethoxybiphenyl-2,2'-diyl]bis (diisopropyl-phosphine) used as the starting material was produced by a Grignard reaction between (S)-(6,6'-dimethoxybiphenyl-2,2'-diyl)bis(phosphonic acid diphenyl ester) and 4-isopropylmagnesium bromide in tetrahydrofuran, followed by reduction of the resulting (S)-(6,6'-dimethoxybiphenyl-2,2'-diyl)bis (diisopropylphosphine oxide) with trichlorosilane in xylene in the presence of tributylamine.

b) The hydrogenation is effected in a 500 ml autoclave which is charged with 8.0 g (31.0 mmol) of dehydrophthaloylic acid, 3.14 g (31.0 mmol) of triethylamine, 150 ml of methanol and the aforementioned catalyst solution. The hydrogenation is carried out at 60°, a constant pressure of 40 bar of pure hydrogen and with vigorous stirring. After 5 hours, the conversion is 99.9% according to GC. The yellow hydrogenation solution is evaporated to a weight of 25 g on a rotary evaporator at 50°/220 mbar. 4.42 ml of 25% hydrochloric acid solution and subsequently 27 ml of water are added dropwise to the residual solution while stirring at 20°–35°. The (S)-acid begins to precipitate at about 25°. The suspension is stirred at 20° for 1 hour and at 0° for 1 hour. After filtration and drying there are obtained 7.7 g (96%) of (S)-acid as almost white crystals with an enantiomeric purity of 96.5% e.e. The e.e. value is determined by HPLC on an α-APG column.

EXAMPLE 19

Production of the methyl 3,4,6,11-tetrahydro-6,11-dioxo-pyridazino[1,2-b]phthalazine-1-carboxylate intermediate (1st variant)

46.4 g (165.3 mmol; purity about 97%) of methyl 1,4,6,11-tetrahydro-6,11-dioxo-pyridazino[1,2-b]phthalazine-1-carboxylate and 1.27 ml (8.27 mmol; 5 mol %; purity about 97%) of 1,8-diaza-bicyclo[5.4.0]undec-7-ene are added in succession to 450 ml of dioxane while gassing with argon and stirring. After increasing the internal temperature to 50° the resulting pale yellow solution is stirred under the same conditions for 16 hours and then cooled to room temperature. The verification of the control of the reaction equilibrium is effected by thin-layer chromatography and GC analysis; according to GC the ratio 3,4,6,11-compound (product): 1,4,6,11-compound (starting material) is 90.3:9.7.

The internal temperature is subsequently lowered to 5°. The reaction mixture is left to stand at 5° for 16 hours without stirring and is then again investigated by thin-layer chromatography and GC, with the result that a 100% conversion 1,4,6,11- →3,4,6,11-compound is established.

The solid is now melted by warming to 18° and the resulting suspension is immediately treated with 6.28 g (33.0 mmol) of p-toluenesulfonic acid hydrate with stirring. The pale beige suspension is stirred for 3 hours while warming slowly to room temperature and 2.72 g (33.2 mmol) of anhydrous sodium acetate are subsequently added thereto. After stirring for one hour, the reaction mixture is evaporated in a high vacuum at a bath temperature of 25°. The moist residue is then dissolved in 300 ml of methylene chloride and the solution is washed with 10% aqueous sodium chloride solution. The combined organic phases are subsequently dried over anhydrous sodium sulfate and the filtrate together with methylene chloride rinsings of the filtered-off sodium sulfate is evaporated to constant weight under reduced pressure (water-jet vacuum) at about 40°. In this manner, there are obtained 45.8 g of a yellow-brown crystallizate which according to GC consists of almost 100% pure methyl 3,4,6,11-tetrahydro-6,11-dioxo-pyridazino[1,2-b]phthalazine-1-carboxylate. The crude yield is almost 100%.

The crude product (45.8 g) is dissolved in 250 ml of hot methylene chloride and the mixture is left to stand at 5° for about 65 hours. After this period, the resulting suspension is filtered and the residue is washed on the filter with 10 ml of n-hexane and then dried in a water-jet vacuum at 50° for about 16 hours. In this manner, there are obtained 40.3 g of yellow crystals, m.p. 160°–161°, which according to GC consist of 100% of the desired product. The yield is 90%.

After evaporation of the mother liquor to dryness there are obtained an additional 6.6 g of methyl 3,4,6,11-tetrahydro-6,11-dioxo-pyridazino[1,2-b]phthalazine-1-carboxylate (almost 100% pure) as yellow-brown crystals.

EXAMPLE 20

Production of the methyl 3,4,6,11-tetrahydro-6,11-dioxo-pyridazino[1,2-b]phthalazine-1-carboxylate intermediate (2nd variant)

a) 363 ml (374 g, 7.47 mol) of hydrazine hydrate are dissolved with stirring in a mixture of 4.4 l of methanol and 500 ml of deionized water. 120 ml (2.10 mol) of glacial acetic acid are now added dropwise to the solution at room temperature within 15 minutes and with continued stirring. The solution is cooled to 4°–6° and at this temperature there is added within 3 hours a solution of 1587 g (6.60 mol; purity about 87% according to GC) of crude methyl 5-bromo-2-oxo-pentanoate in 900 ml of methanol, whereby after the addition of about three quarters of this solution 200 ml of 3M aqueous potassium carbonate solution are added portionwise in such a manner that the pH value of the reaction mixture is between 4 and 7. After completion of the addition of the methyl 5-bromo-2-oxo-pentanoate solution, the internal temperature is increased to 62°–63° (reflux) within 30 minutes with continued stirring and the pH value is held between 4 and 7 by the simultaneous addition of 1.1 l of a 3M solution of potassium carbonate in deionized water. After completion of the addition of the potassium carbonate solution, the reaction mixture is stirred at reflux temperature for an additional 2.5 hours.

For the work-up, the reaction mixture is concentrated at 40° in a water-jet vacuum, whereby a total of about 5 l of methanol are distilled off. The residual brown suspension is diluted with 1 l of water, whereby the salt-like precipitate is dissolved, and the aqueous solution is washed five times with 3 l of ethyl acetate each time. Each organic phase is now washed with 1 l of water and the combined organic phases (about 5 l) are then evaporated to constant weight at 45° in a water-jet vacuum. 1093 g of a yellow, crystalline mass are obtained. This crude product is dissolved in a mixture of 1 l of ethyl acetate and 2 l of toluene and the resulting solution is washed twice with 250 ml of semi-saturated aqueous sodium chloride solution each time, filtered through Hyflo® (filter aid) and then evaporated. By washing with water, there are removed polar, not precisely identified byproducts, which would otherwise detrimentally affect the purity of the end product.

Subsequently, the residue is treated with 500 ml of a 1:1 mixture of toluene and n-hexane, the resulting suspension is stirred briefly at 50° and cooled to room temperature. The crystals are then removed by filtration under suction. The filter cake is washed with a mixture of 250 ml of toluene and 250 ml of n-hexane and dried to constant weight at 50° in a water-jet vacuum. There are thus obtained 610.7 g of slightly yellowish crystals of the desired methyl 1,4,5,6-tetrahydro-3-pyridazinecarboxylate. The filtrate is, in turn, evaporated and the residue is treated with 200 ml of a 1:1 mixture of toluene and n-hexane, stirred briefly at room temperature and filtered. The filter cake is washed with a mixture of 10 ml of toluene and 60 ml of n-hexane and dried at 50° in a water-jet vacuum, whereupon there are obtained an additional 45.3 g of yellow crystals of the intermediate.

The filtrate is evaporated to dryness and the red-black, oily residue (373 g) is subsequently distilled in a molecular evaporator at 128°/0.04–0.06 mbar. The partially crystalline, yellow distillate (176 g) is then dissolved in 750 ml of ethyl acetate. The resulting solution is washed with 100 ml of semi-saturated, aqueous sodium chloride solution and evaporated to dryness. The residue is treated with 150 ml of a 1:1 mixture of toluene and n-hexane, stirred for a short time and then filtered, and the filter cake is washed with a mixture of 25 ml of toluene and 25 ml of n-hexane and dried at 50° in a water-jet vacuum. There are obtained an additional 42.0 g of yellow crystals of methyl 1,4,5,6-tetrahydro-3-pyridazine-carboxylate.

The total yield of methyl 1,4,5,6-tetrahydro-3-pyridazinecarboxylate as yellowish crystals is 698 g, 74% of the theoretical yield; pure according to thin-layer chromatography and GC.

b) A mixture of 213.2 g (1.50 mol) of methyl 1,4,5,6-tetrahydro-3-pyridazinecarboxylate, produced according to the procedure described in a), 240 g (1.62 mol) of phthalic anhydride and 2 l of methylene chloride is heated at 40°, reflux temperature, for 17 hours, with stirring. The resulting suspension is cooled, treated at 17°–21° within 110 minutes with a solution of 140 ml (1.29 mol) of thionyl chloride in 100 ml of methylene chloride and subsequently left to react for 2 hours.

For the work-up, the reaction mixture is concentrated to a large extent in a water-jet vacuum at 40° and the solid residue is treated with 1 l of methanol, whereby there is obtained a yellow suspension which can be stirred well. This suspension is now evaporated and the residue is treated twice with 500 ml of methanol each time and evaporated each time. The resulting yellow crystal slurry is then suspended in 150 ml of methanol and the suspension is filtered.

Finally, the filter cake is suspended twice with 300 ml of methanol each time, vacuum dried well each time and dried at 50° in a water-jet vacuum for about 16 hours. In this manner, there are obtained 368.3 g (90% of the theoretical yield) of methyl 3,4,6,11-tetrahydro-6,11-dioxo-pyridazino[1,2-b]phthalazine-1-carboxylate as a yellowish homogeneous crystalline powder, m.p. 156°–157°. The product is found to be pure according to thin-layer chromatography.

EXAMPLE 21

Production of 3,4,6,11-tetrahydro-6,11-dioxo-pyridazino[1,2-b]phthalazine-1-carboxylic acid 75 g (275 mmol) of methyl 3,4,6,11-tetrahydro-6,11-dioxo-pyridazino[1,2-b]phthalazine-1-carboxylate (produced according to the procedure described in Example 19 or 20) are dissolved in 300 ml of acetic acid while gassing with argon and stirring. The solution is then treated with 5 g of Darco® KB-B (active charcoal in powder form; ICI), the internal temperature is increased to about 65°and the resulting suspension is stirred at this temperature for 30 minutes. The warm suspension is subsequently filtered through about 10 g of Dicalite® (filter aid; Dicalite Europe Nord S.A.) and the Dicalite® pad is washed with 150 ml of acetic acid. The combined acetic acid phases are partly evaporated at 50°–55° in a water-jet vacuum and the residual yellow solution is diluted with 80 ml of acetic acid. This solution is now treated with 1 ml (11.4 mmol) of trifluoromethanesulfonic acid and the solution is stirred at 102° for 20 hours. The initially clear, yellow solution becomes turbid after about 30 minutes, whereupon a pale precipitate is formed which gradually becomes thicker, namely within a few minutes. The suspension remains well-stirrable throughout.

For the work-up, the reaction mixture is cooled to 25°, treated with 400 ml of deionized water and stirred at room temperature for 1.5 hours. The suspension is now filtered and the filter cake is vacuum dried well. Finally, the filter cake is washed well on the filter three times with 180 ml of deionized water each time and then twice with 250 ml of methanol each time, vacuum dried well each time and dried at 55° for about 16 hours in a drying oven under a water-jet vacuum. In this manner, there are obtained 62.6 g, 88% of the theoretical yield, of 3,4,6,11-tetrahydro-6,11-dioxo-pyridazino [1,2-b]phthalazine-1-carboxylic acid, which has a purity of 98 area percent according to GC.

We claim:

1. A process for the preparation of a compound of the formula:

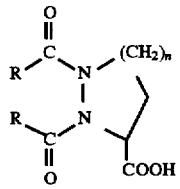

I wherein each R, independently, is alkyl, arylmethyl, aryl, alkoxy, arylmethoxy or aryloxy, or both R's together are 1,2-phenylene and n is 1 or 2, in the (S)- or (R)-form, which process comprises asymmetrically hydrogenating the corresponding 3-carboxy-3-pyrazoline or 3-carboxy-1,2,5,6-tetrahydropyridazine derivative of the formula

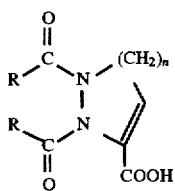

II where R and n have the significance's given above, or a salt thereof, in the presence of an optically active ruthenium-diphosphine complex of the formula:

$$Ru(X^1)_2L \qquad \qquad III$$

or $$[Ru(X^2)_{2-m}X^3L](X^4)_m \qquad \qquad IV$$

wherein $X^1$ is a halide, an anion A—COO$^\ominus$ or an anion A—SO$_2$O$^\ominus$, $X^2$ is a halide, $X^3$ is benzene, hexamethylbenzene or p-cymene, $X^4$ is a halide, BF$_4^\ominus$, ClO$_4^\ominus$ or B(phenyl)$_4^\ominus$, m is the number 1 or 2, A is lower alkyl halogenated lower alkyl or aryl and L is an optically active atropisomeric diphosphine ligand selected from a group of compounds consisting of a compound of the formula:

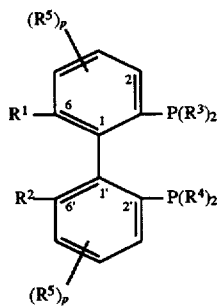

V and a compound of the formula

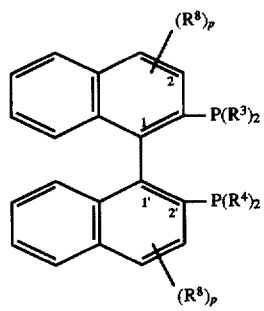

VI wherein $R^1$ and $R^2$, independently, are lower alkyl, lower alkoxy, di(lower alkyl)amino, hydroxy, protected hydroxy, hydroxymethyl or protected hydroxymethyl or $R^1$ and $R^2$ taken together are a divalent group:

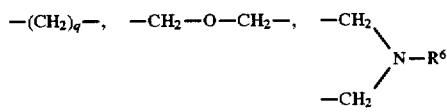

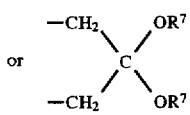

$R^3$ and $R^4$, independently, are lower alkyl, C$_{3-7}$-cycloalkyl, optionally substituted phenyl, a five-membered heteroaromatic or a group of the formula

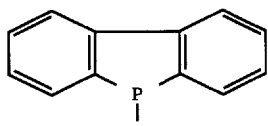

$R^5$ is lower alkyl or lower alkoxy, $R^6$ is lower alkyl, optionally substituted phenyl or optionally substituted benzyl, $R^7$ is lower alkyl or both $R^7$'s taken together are di-or trimethylene $R^8$ is halogen, hydroxy, methyl, ethyl, amino, acetamido, nitro or sulfo, p is zero or the number 1, 2 or 3 and q is the number 3,4 or 5.

2. A process, according to claim 1, wherein n is 2.

3. A process, according to claim 2, wherein 3,4,6,11-tetrahydro-6,11-diozo-pyridazino[1,2-b]phthalazine-1-carboxylic acid is hydrogenated to (S)-1,2,3,4,6,11-hexahydro-6,11-dioxo-pyridazino[1,2-b]phthalazine-1-carboxylic acid.

4. A process according to claim 1, wherein the hydrogenation is in the presence of a ruthenium-diphosphine complex of the formula $$Ru(X^1)_2L \qquad \qquad III$$

wherein L is selected from the group consisting of:

(S)-(6,6'-dimethylbiphenyl-2,2'-diyl)bis(diphenyl-phosphine);

(S)-(6,6'-dimethoxybiphenyl-2,2'-diyl)bis(diphenyl-phosphine);

(S)-(6,6'-dimethoxybiphenyl-2,2'-diyl)bis(di-(3,4,5-trimethoxyphenyl)phosphine];

(S)-(6,6'-dimethylbiphenyl-2,2'-diyl)bis(di-(2-thienyl)phosphine];

(S)-(4,4',5,5',6,6'-hexamethoxybiphenyl-2,2'-diyl)bis-(diphenylphosphine);

(S)-(5,5',6,6'-tetramethoxybiphenyl-2,2'diyl)bis-(diphenyl-phosphine);

(S)-(5,7-dihydro-dibenz[c,e]oxepin-1,11-diyl)bis-(diphenyl-phosphine);

(S)-(6,6'-Dimethoxybiphenyl-2,2'-diyl)bis[di-(p-tolyl)phosphine];

(S)-(6,6'-dimethylbiphenyl-2,2'-diyl)bis[di-(p-tolyl)phosphine];

(S)-(1,1'-binaphthyl-2,2'-diyl)bis[di-(p-tolyl)-phosphine;

(S)-(6,6'-dimethoxybiphenyl-2,2'-diyl)bis(dicyclohexyl-phosphine).

5. A process according to claim 1, wherein the hydrogenation is in the presence of a catalyst solution comprising di(η²acetato)-(η⁴-cycloocta-1,5-diene)ruthenium (II) and [(S)-6,6'-dimethoxybiphenyl-2,2'-diyl]bis(diisopropylphosphine).

6. A process, according to claim 1, wherein 3,4,6,11-tetrahydro-6,11-dioxo-pyridazino[1,2-b]phthalazine-1-carboxylic acid is hydrogenated to (R)-1,2,3,4,6,11-hexahydro-6,11-dioxo-pyridazino[1,2-b]phthalazine-1-carboxylic acid.

7. A process, according to claim 6, wherein the hydrogenation is in the presence of an optically active ruthenium-diphosphine complex of the formula:

   III wherein L is (R)-(6,6'-dimethoxybiphenyl-2,2'-diyl)bis(diphenylphosphine).

8. A process, according to claim 1, wherein the hydrogenation is carried out at a temperature of between about 0° C. to about 150° C.

9. A process, according to claim 8, wherein the hydrogenation is carried out at a pressure of about 1 to about 100 bar.

10. A process, according to claim 1, wherein a percentage molar ratio of ruthenium in the catalyst to a compound of formula II or its salt is between about 0.0005 to about 5.

* * * * *